(12) United States Patent
Goettel et al.

(10) Patent No.: US 6,716,257 B2
(45) Date of Patent: Apr. 6, 2004

(54) BRIDGED DIAMINOPYRAZOLE COMPOUNDS AND DYE COMPOSITIONS CONTAINING SAME

(75) Inventors: Otto Goettel, Marly (CH); Aline Pirrello, Givisiez (CH); André Hayoz, Senèdes (CH); Emmanuel Morand, Neyruz (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 10/017,575

(22) Filed: Dec. 14, 2001

(65) Prior Publication Data

US 2002/0170125 A1 Nov. 21, 2002

(30) Foreign Application Priority Data

Mar. 1, 2001 (DE) .......................... 101 09 807

(51) Int. Cl.⁷ .................. A61K 7/13; C07D 403/06; C07D 403/10; C07D 401/14
(52) U.S. Cl. ................ 8/409; 8/405; 8/429; 548/365.1; 548/365.4; 548/364.4; 546/256
(58) Field of Search .............. 548/365.1, 365.4; 8/429, 409, 405

(56) References Cited

U.S. PATENT DOCUMENTS

| | | | |
|---|---|---|---|
| 3,414,580 A | 12/1968 | Hoehn | |
| 6,099,592 A | 8/2000 | Vidal et al. | 8/406 |
| 6,118,008 A | 9/2000 | Malle et al. | 548/371.4 |
| 6,338,741 B1 | 1/2002 | Vidal et al. | 548/373.1 |
| 6,361,571 B1 * | 3/2002 | Goettel et al. | 8/405 |

FOREIGN PATENT DOCUMENTS

| | | |
|---|---|---|
| DE | 42 34 885 A1 | 4/1994 |
| DE | 43 34 887 A1 | 4/1994 |
| EP | 0 375 977 A1 | 7/1990 |
| EP | 0 740 931 A1 | 11/1996 |
| WO | 99/11231 | 3/1999 |

OTHER PUBLICATIONS

CA 137:206178, Javet et al. 2002.*
CA 137:206177, Javet et al. 2002.*

* cited by examiner

Primary Examiner—Evelyn Mei Huang
(74) Attorney, Agent, or Firm—Michael J. Striker

(57) ABSTRACT

The new diaminopyrazole compounds are bridged 4,5-diaminopyrazole compounds or salts thereof. These diaminopyrazole compounds have the formula (I):

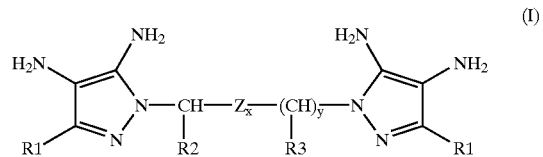

wherein R1 represents hydrogen, a $C_1$- to $C_6$-alkyl, a $C_1$- to $C_4$-hydroxyalkyl, a $C_1$- to $C_4$-aminoalkyl, a $C_1$- to $C_8$-alkylamino, a di($C_1$- to $C_8$-alkyl)amino, a $C_1$- to $C_4$-alkylamino-($C_1$- to $C_4$-alkyl), a di($C_1$- to $C_4$-alkylamino)-$C_1$- to $C_4$-alkyl, an aryl or a heteroaryl; R2 and R3 each represent hydrogen, a straight-chain or branched $C_1$- to $C_6$-alkyl, an aryl, a heteroaryl, a carboxylic acid, a carboxylic acid ester, an unsubstituted or substituted carboxylic acid amide, a hydroxy or a $C_1$- to $C_4$-hydroxyalkyl group, or R2 and R3 together represent a $C_1$- to $C_6$-alkylene group; Z represents a $C_1$- to $C_{10}$-alkyl diradical, optionally interrupted by a heteroatom, an aromatic or heteroaromatic diradical, optionally substituted with a hydroxy group, a $C_1$- to $C_6$-alkyl group and/or is subjected to a benzocondensation once or twice; or Z is —Ar(Alk)$_n$—Ar—, wherein Ar represents an arylene group or a heteroarylene group, Alk represents a —CH$_2$— group and n is 0 to 6; and x and y are 0 or 1.

16 Claims, No Drawings

BRIDGED DIAMINOPYRAZOLE COMPOUNDS AND DYE COMPOSITIONS CONTAINING SAME

BACKGROUND OF THE INVENTION

The subject matter of the present invention includes new 4,5-diaminopyrazole compounds and their physiologically compatible salts with organic or inorganic acids. The subject matter of the present invention also includes dye compositions containing these new compounds as dyestuff precursor compounds.

Oxidation dyestuffs have been important in the field of traditional hair dyeing for a long time. The effective dyeing agent is produced by reaction of certain developer and coupler substances in the presence of an oxidizing agent. Hair dye compositions for dyeing hair natural color shades are of special significance. Besides those dye compositions combinations of suitable oxidation dye precursor compounds are used to produce currently fashionable color nuances and accents. Currently brown shades with outstanding aubergine or copper tones, especially glowing red tones that deviate from natural colors, can be produced.

Oxidation dyestuffs, which are used for treatment of human hair, have very stringent requirements besides the requirements for producing certain predetermined color effects. The dyestuff must be both toxicologically and dermatologically unobjectionable and also not sensitizing. A broad palette of different color shades and nuances are required, which must be obtained by suitable combination of appropriate developer and coupler components. The hair dyeing compositions obtained should have good wash-fastness, light-fastness, sweat-fastness, permanent wave-fastness, acid-fastness, base-fastness and friction-fastness. In each case these hair dye compositions must remain stable under the common current daily conditions for at least four to six weeks.

In the past 4-aminophenol was the predominant developer used to cover the increasingly important red range. Pyridine derivatives and pyrimidine derivatives, which generally are not satisfactory for dyeing, have also been employed because of considerations regarding the physiological compatibility of 4-aminophenol. A significant improvement in the color stability, especially in the red range, was obtained by the exchange of p-aminophenol by the 4,5-diaminopyrazole compounds described in German Patent Applications DE-OS 42 34 885, DE-OS 42 34 887 and EP-OS 0 375 977. The manufacture of these latter dye compounds by the methods described in those applications is however, in part, very expensive and requires, in part, starting materials, which are expensive and not widely available. 4,5-diaminopyrazoles substituted in the 3 position are known from EP-OS 0 740 931. These compounds however must be made, in part, according to an expensive method, since components, especially C3 components, are not readily available. The pyrazoles described in EP-OS 0 740 931 are also not entirely satisfactory in regard to the attainable color palette and color saturation.

While most oxidation dyestuffs are characterized by hardly any weakening or impairment on undamaged hair, serious differences result when they are used on damaged hair. The hairstylist knows from his daily practice that dyestuffs are not absorbed uniformly on the hair to be dyed. While the hair roots are usually intact, the hair tips are generally damaged because of the effects of weather, frequent washing and combing as time goes on. The damage increases from the roots to the tips. A non-uniform color is thus produced from the roots to the tips when the hair is dyed because of the non-uniform condition of the hair from the roots to the tips. An additional problem is that the absorbed dyestuffs are more easily washed from the damaged part of the hair than from the undamaged part of the hair. As a result after a few washings of the dyed hair the differences in the color of the dyed damaged part of the hair and the dyed undamaged part of the hair are more clearly visible.

SUMMARY OF THE INVENTION

Thus there is a great long-standing need for new dye precursor compounds suitable for oxidative dye systems for coverage of the red range, which provide a considerably improved color stability against shampooing on hair of different quality, especially on hair that has been damaged by permanent shaping and bleaching, besides good absorption properties. It is an object of the present invention to provide these new dye precursor compounds.

Certain special new bridged pyrazole compounds attain this object in an outstanding manner.

The subject matter of the present invention thus includes the bridged 4,5-diaminopyrazole compounds of formula (I) or their salts with organic or inorganic acids:

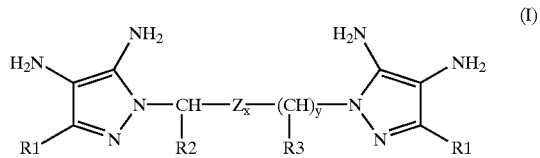

wherein

R1 represents hydrogen, a straight-chain or branched $C_1$- to $C_6$-alkyl group, a $C_1$- to $C_4$-hydroxyalkyl group, a $C_1$- to $C_4$-aminoalkyl group, a $C_1$- to $C_8$-alkylamino group, a di($C_1$- to $C_8$-alkyl)amino group, a $C_1$- to $C_4$-alkylamino-($C_1$- to $C_4$-alkyl) group or a di($C_1$- to $C_4$-alkylamino)- $C_1$- to $C_4$-alkyl group, an aryl group or a heteroaryl group;

R2 and R3, independently of each other, are the same or different and each represent hydrogen, a straight-chain or branched $C_1$- to $C_6$-alkyl group, an aryl group, a heteroaryl group, a carboxylic acid group, a carboxylic acid ester group, an unsubstituted or substituted carboxylic acid amide group, a hydroxy group or a $C_1$- to $C_4$-hydroxyalkyl group, or R2 and R3 together represent an unsubstituted or substituted $C_1$- to $C_6$-alkylene group;

Z represents a $C_1$- to $C_{10}$-alkyl diradical, which is optionally interrupted by a heteroatom, for example by a nitrogen atom, an oxygen atom or a sulfur atom, an aromatic or heteroaromatic diradical, which may be substituted optionally with a hydroxy group or a $C_1$- to $C_6$-alkyl group and/or may be subjected to a benzocondensation once or twice; or a diradical of formula —Ar(Alk)$_n$—Ar—, wherein Ar represents an arylene group or a heteroarylene group (especially a phenylene group or a pyridylene group), which may optionally be substituted, Alk represents a —CH$_2$— group and n represents a number from 0 to 6; and x and y independently of each other represent 0 or 1.

The following bridged pyrazole compounds of formula (I) are, for example, suitable:

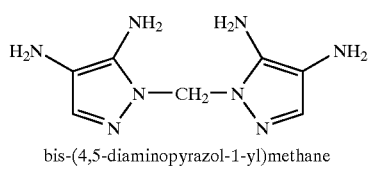
bis-(4,5-diaminopyrazol-1-yl)methane (I-a)

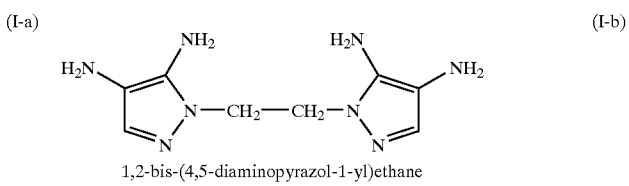
1,2-bis-(4,5-diaminopyrazol-1-yl)ethane (I-b)

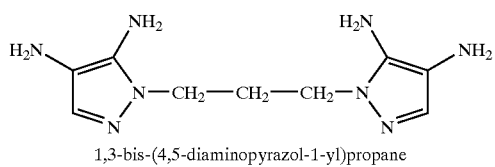
1,3-bis-(4,5-diaminopyrazol-1-yl)propane (I-c)

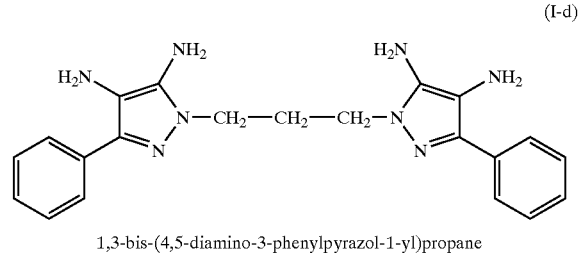
1,3-bis-(4,5-diamino-3-phenylpyrazol-1-yl)propane (I-d)

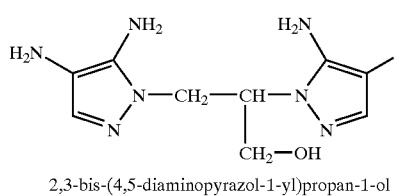
2,3-bis-(4,5-diaminopyrazol-1-yl)propan-1-ol (I-e)

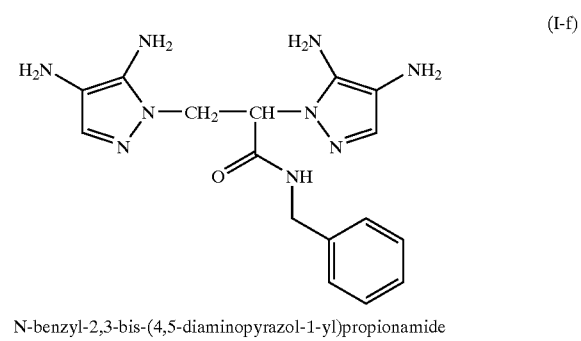
N-benzyl-2,3-bis-(4,5-diaminopyrazol-1-yl)propionamide (I-f)

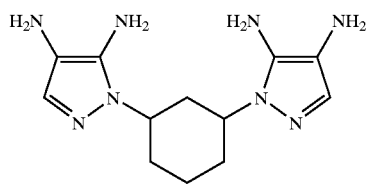
1,3-bis(4,5-diaminopyrazol-1-yl)cyclohexane (I-g)

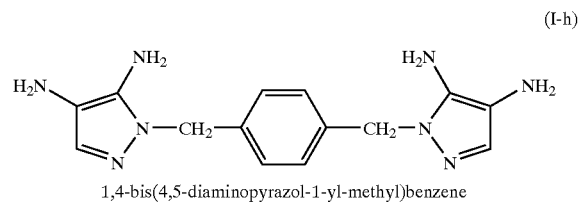
1,4-bis(4,5-diaminopyrazol-1-yl-methyl)benzene (I-h)

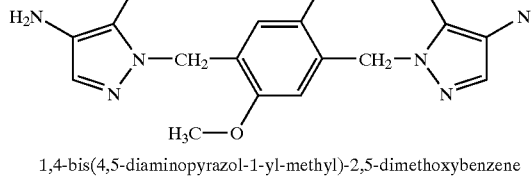
1,4-bis(4,5-diaminopyrazol-1-yl-methyl)-2,5-dimethoxybenzene (I-i)

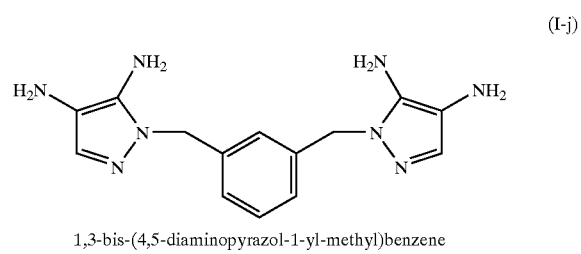
1,3-bis-(4,5-diaminopyrazol-1-yl-methyl)benzene (I-j)

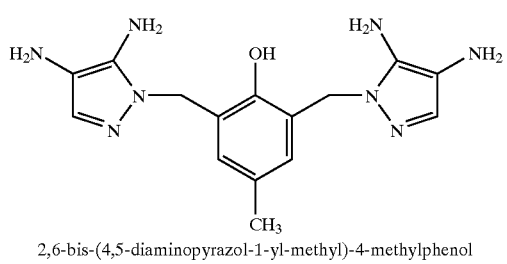
2,6-bis-(4,5-diaminopyrazol-1-yl-methyl)-4-methylphenol (I-k)

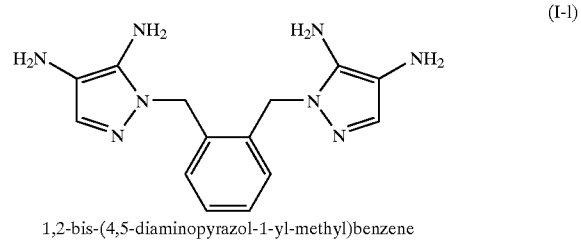
1,2-bis-(4,5-diaminopyrazol-1-yl-methyl)benzene (I-l)

-continued

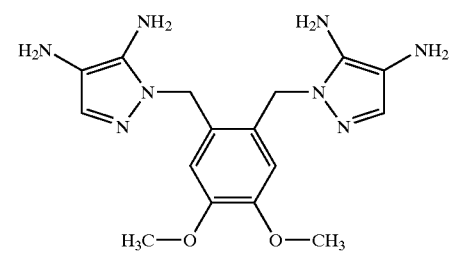

1,2-bis-(4,5-diaminopyrazol-1-yl-methyl)-4,5-dimethoxybenzene (I-m)

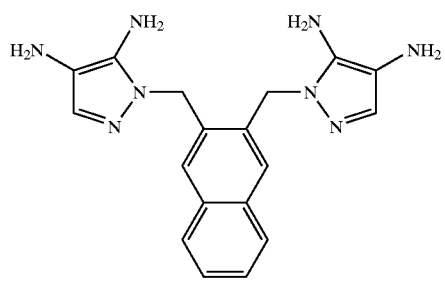

2,3-bis-(4,5-diaminopyrazol-1-yl-methyl)naphthalene (I-n)

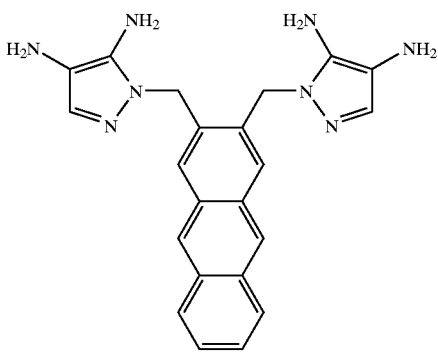

2,3-bis-(4,5-diaminopyrazol-1-yl-methyl)anthracene (I-o)

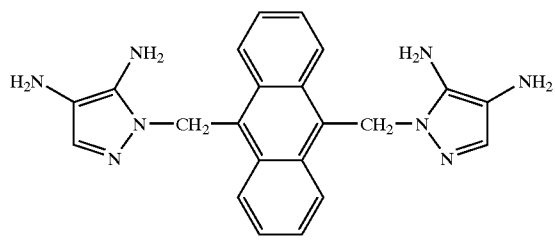

9,10-bis-(4,5-diaminopyrazol-1-yl-methyl)anthracene (I-p)

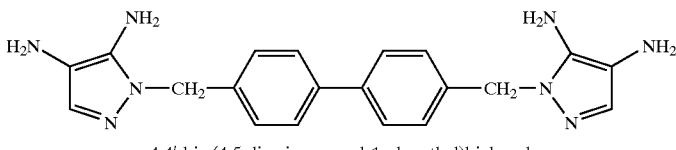

4,4'-bis-(4,5-diaminopyrazol-1-yl-methyl)biphenyl (I-q)

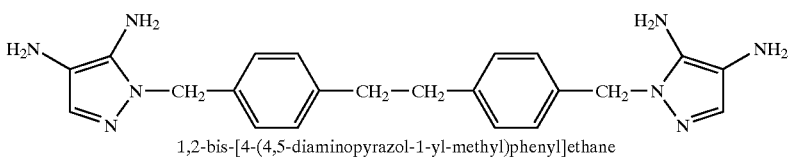

1,2-bis-[4-(4,5-diaminopyrazol-1-yl-methyl)phenyl]ethane (I-r)

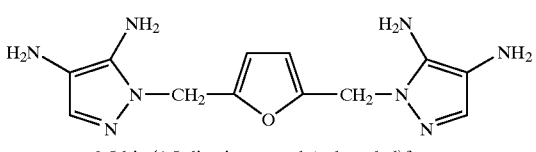

2,5-bis-(4,5-diaminopyrazol-1-yl-methyl)furan (I-s)

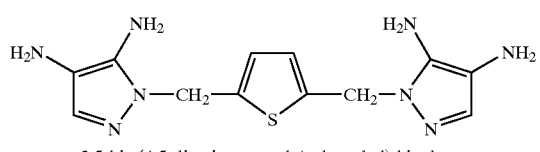

2,5-bis-(4,5-diaminopyrazol-1-yl-methyl)thiophene (I-t)

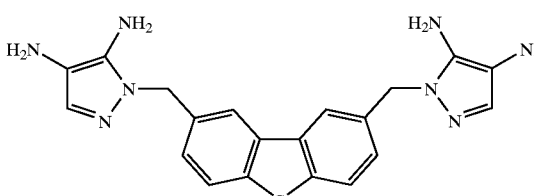

2,8-bis-(4,5-diaminopyrazol-1-yl-methyl)dibenzothiophene (I-u)

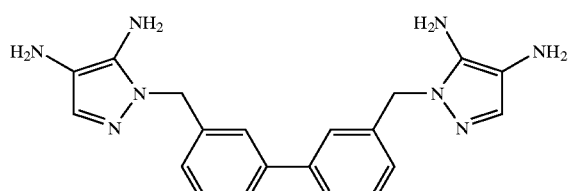

4,4'-bis-(4,5-diaminopyrazol-1-yl-methyl)-[2,2']bipyridyl (I-v)

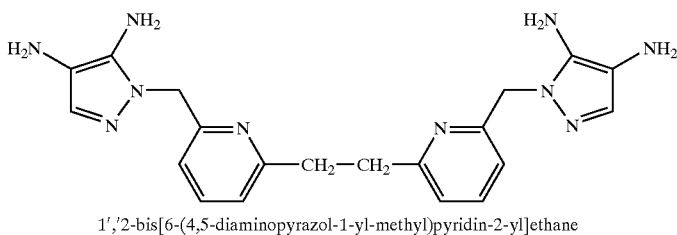

1',2'-bis[6-(4,5-diaminopyrazol-1-yl-methyl)pyridin-2-yl]ethane

Compounds of the general formula (I), in which R1 is a hydrogen atom, a methyl group, a phenyl group, a thienyl group or a furyl group; R2 and R3, independently of each other, each represent a hydrogen atom, a phenyl group, a carboxylic acid amide group or a hydroxymethyl group; Z represents an unsubstituted alkylene diradical, phenylene diradical or heteroaryl diradical, and x and y each represent, independently of each other, 0 or 1, are especially preferred as dye compounds of the invention and in the dye compositions of the invention.

Compounds of formula (I), in which R1 to R3 each represent a hydrogen atom; Z represents an unsubstituted alkylene diradical, phenylene diradical or heteroaryl diradical, and x and y each represent, independently of each other, 0 or 1, are especially preferred as dye compounds of the invention and in the dye compositions of the invention.

The compounds of formula (I) can be made with different methods.

One possible synthesis schema 1 is described hereinbelow. First two equivalents of 3,5-dibromo-4-nitropyrazole are bridged with a dihalogenide. After conversion to the corresponding 5-benzylamino compound and subsequent catalytic hydrogenation one obtains the corresponding 4,5-diaminopyrazole of the general formula (I).

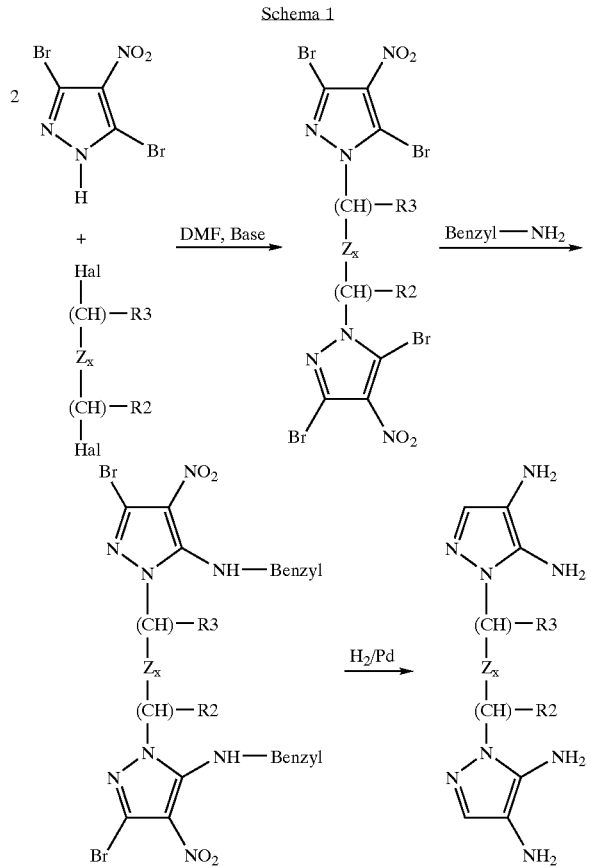

However in the case of certain embodiments the preparative schema 2 is advantageous. In the method of schema 2 first cyanoethyl hydrazine is reacted with dialdehydes or diketones to form the corresponding dihydrazones. Subsequently the dihydrazones so obtained are cyclized to form the bridged 5-aminopyrazoles. The intermediate steps in the method are performed, for example, according to the procedure set forth in FR-A 1 403 372. The subsequent introduction of the second pyrazole amino group into position 4, which for example is possible by azo coupling or nitrosation, similarly makes 4,5-diaminopyrazoles of the general formula (I) available. This synthesis schema

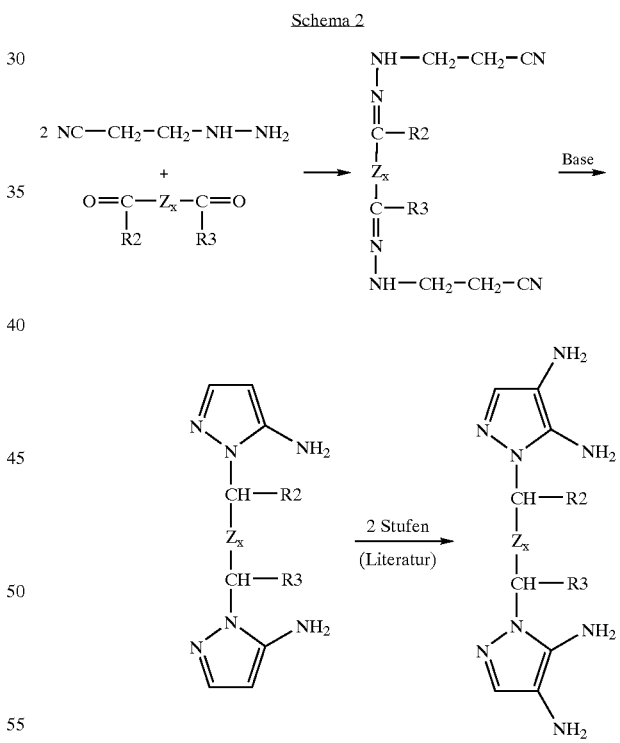

preferably starts with the aldehydes.

The 5-benzylamino-3-bromo compounds from schema 1 could be employed for introduction of a substituent in the 3 position of the pyrazole. Ideally this can occur according to Schema 3, for example, by Suzuki coupling, in which additional coupling reactions are conceivable.

Schema 3

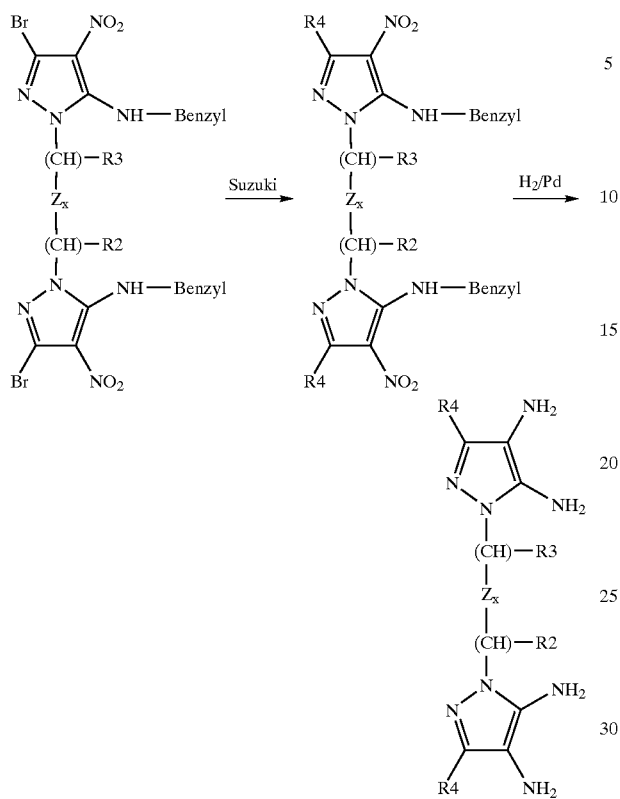

Because of the oxidation sensitivity of the 4,5-diaminopyrazole compounds according to the invention the compounds of formula (I) are preferably isolated as free acid adducts instead of free bases for reasons of improved handling. The salts so obtained are predominantly oxygen insensitive. In organic or organic acids can be used for this purpose. For example, citric acid, tartaric acid and especially hydrochloric and sulfuric acids are preferable.

The compounds of formula (I) are predominantly suitable as dye precursor compounds in an oxidative system for dyeing keratin fibers. Although the compounds of formula (I) are especially suitable for dyeing keratin fibers, for example wool, silk or hair, especially human hair, they can also be used for dyeing other natural or synthetic fibers, especially cotton or nylon 66.

The subject matter of the present invention also includes a composition for oxidative dyeing of keratin fibers, especially hair, which is characterized by a content of at least one 4,5-diaminopyrazole of the general formula (I), or a salt thereof with an organic or inorganic acid.

The 4,5-diaminopyrazole of formula (I) is contained in the dye compositions according to the invention in an amount of about 0.005 to 20 percent by weight. However the preferred amount of the 4,5-diaminopyrazole of formula (I) in the dye composition according to the invention is from about 0.01 to 10 percent by weight and especially from about 0.1 to 6 percent by weight.

The compounds of formula (I) can be used both alone and also in combination with the known developer and/or coupler substances, which usually are found in oxidative dye system for dyeing fiber materials.

The following known coupler substances are particularly suited for the composition according to the invention:
N-(3-dimethylaminophenyl)-urea, 2,6-diamino-pyridine, 2-amino-4-[(2-hydroxyethyl)amino]-anisole, 2,4-diamino-1-fluoro-5-methyl-benzene, 2,4-diamino-1-methoxy-5-methylbenzene, 2,4-diamino-1-ethoxy-5-methyl-benzene, 2,4-diamino-1-(2-hydroxyethoxy)-5-methylbenzene, 2,4-di[(2-hydroxyethyl)amino]-1,5-dimethoxy-benzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)-benzene, 2,4-diamino-1-(3-hydroxypropoxy)-benzene, 2,4-diamino-1-(3-methoxypropoxy)-benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)-phenol, 3-[(2-hydroxyethyl)amino]-aniline, 3-[(2-aminoethyl)-amino]-aniline, 1,3-di(2,4-diaminophenoxy)-propane, di(2,4-diaminophenoxy) methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methyl-phenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]-acetamide, 5-[(2-hydroxyethyl)-amino]-2-methylphenol, 3-[(2-hydroxy-ethyl)amino]-phenol, 3-[(2-methoxyethyl)amino]-phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)-amino]-2-methylphenol, 3-[(2-hydroxyethyl)-amino]-2-methylphenol, 2-amino-3-hydroxypyridine, 5-amino-4-chloro-2-methylphenol, 1-naphthol, 1,5-dihydroxynapthalene, 1,7-dihydroxynapthalene, 2,3-dihydroxynapthalene, 2,7-dihydroxynapthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 1,3-dihydroxy-2,4-dimethylbenzene, 3,4-methylendioxyphenol, 3,4-methylendioxyaniline, 5-[(2-hydroxyethyl)amino]-1,3-benzodioxol, 6-bromo-1-hydroxy-3,4-methylendioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazoleone, 5,6-dihydroxyindole, 5,6-dihydroxyindoleine, 4-hydroxyindole, 5-hydroxyindole, 6-hydroxyindole, 7-hydroxyindole and 2,3-indoleindione, or their salts.

For production of natural and fashionable red shades it is especially advantageous to combine the compounds of formula (I) with additional developer substances. The additional developer substances include p-phenylenediamines, p-aminophenols and other 4,5-diaminopyrazoles or their salts.

Particularly the following additional developer substances are preferred for inclusion in the compositions of the invention:
1,4-diaminobenzene (p-phenylendiamine), 1,4-diamino-2-methylbenzene (p-toluylenediamine), 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenylaminoaniline, 4-dimethylaminoaniline, 4-diethylaminoaniline, 4-[di(2- hydroxyethyl)amino]aniline, 4-[(2-methoxyethyl)amino] aniline, 4-[(3-hydroxypropyl)amino]-aniline, 1,4-diamino-2-(2-hydroxyethyl)benzene, 1,4-diamino-2-(1-hydroxyethyl)benzene, 1,4-diamino-2-(1-methylethyl) benzene, 1,3-bis-[(4-aminophenyl)-(2-hydroxyethyl) amino]-2-propanol, 1,8-bis-(2,5-diaminophenoxy)-3,6-dioxaoctane, 4-aminophenol, 4-amino-3-methylphenol, 4-methylaminophenol, 4-amino-2-(aminomethyl)phenol, 4-amino-2-[(2-hydroxyethyl)-amino]methyl-phenol, 4-amino-2-(methoxymethyl)phenol, 4-amino-2-(2-hydroxyethyl)phenol, 5-aminosalicylic Acid, 2,5-diaminopyridine, 2,4,5,6-tetraaminopyrimidine, 2,5,6-triamino-4-(1H)pyrimidone, 4,5-diamino-1-(2-hydroxy-ethyl) -1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 4,5-diamino-3-methyl-1-phenyl-1H-pyrazole, 4,5-diamino-1-(2-hydroxyethyl)-3-methyl-1H-pyrazole, 2-aminophenol, 2-amino-6-methylphenol and 2-amino-5-methylphenol or their salts.

The known developer substances and coupler substances are contained in the composition according to the invention in a total amount of from about 0.01 to 20 percent by weight, preferably about 0.2 to 6 percent by weight.

The compounds of formula (I) understandably can be employed in combination with conventional anionic, cationic, zwitterionic or nonionic dyestuffs.

Suitable anionic dyestuffs include, for example, the following:

6-hydroxy-5-[(4-sulfophenyl)azo]-2-naphthalene sulfonic acid disodium salt (Cl 15985; Food Yellow No. 3; FD&C Yellow No. 6), 2,4-dinitro-1-naphthol-7-sulfonic acid disodium salt (Cl 10316; Acid Yellow No. 1; Food Yellow No. 1), 2-(indan-1,3-dion-2-yl)quinoline-x,x-sulfonic acid (mixture of mono and disulfonic acid) (Cl 47005; D&C Yellow No. 10; Food Yellow No. 13, Acid Yellow No. 3), 5-hydroxy-1-(4-sulfophenyl)-4-[(4-sulfophenyl) azo]-pyrazole-3-carboxylic acid trisodium salt (Cl 19140; Food Yellow no. 4; Acid Yellow No. 23), 9-(2-carboxyphenyl)-6-hydroxy-3H-xanthen-3-one (Cl 45350; Acid Yellow No. 73; D&C Yellow No. 8), 5-[(2,4-dinitrophenyl)amino]-2-phenylaminobenzene sulfonic acid sodium salt(Cl 10385; Acid Orange No. 3), 4-[(2,4-dihydroxyphenyl)azo]-benzene sulfonic acid monosodium salt(Cl 14270; Acid Orange No. 6), 4-[(2-hydroxynaphth-1-yl)azo]-benzene sulfonic acid sodium salt(Cl 15510; Acid Orange No. 7), 4-[(2,4-dihydroxy-3-[(2,4-dimethylphenyl)azo]phenyl)azo-benzene sulfonic acid sodium salt(Cl 20170; Acid Orange No. 24), 4-hydroxy-3-[(4-sulfonaphthalen-1-yl)azo]-1-napthalene sulfonic acid disodium salt (Cl 14720; Acid Red No. 14), 6-hydroxy-5-[(4-sulfonaphth-1-yl)azo]-2,4-napthalene-disulfonic acid trisodium salt(Cl 16255; Ponceau 4R; Acid Red No. 18), 3-hydroxy-4-[(4-sulfonaphth-1-yl) azo]-2,7-napthalene-disulfonic acid trisodium salt (Cl 16185; Acid Red No. 27), 8-amino-1-hydroxy-2-(phenylazo)-3,6-napthalene disulfonic acid disodium salt (Cl 17200; Acid Red No. 33), 5-(acetyl-amino)-4-hydroxy-3-[(2-methyl-phenyl) -azo]-2,7-napthalene disulfonic acid disodium salt (Cl 18065; Acid Red No. 35), 2-(3-hydroxy-2,4,5,7-tetraiodo-dibenzopyran-6-on-9-yl)-benzoic acid -disodium salt (Cl 45430;Acid Red No. 51), N-[6-(diethylamino)-9-(2,4-disulfophenyl) -3H-xanthen-3-yliden]-N-ethyl-ethanaminium hydroxide, inner salt, sodium salt (Cl 45100; Acid Red No. 52), 8-[(4-(phenylazo)-phenyl)azo]-7-naphthol-1,3-disulfonic acid disodium salt (Cl 27290; Acid Red No. 73), 2',4',5', 7'-tetrabromo-3',6'-dihydroxyspiro[isobenzofuran-1(3H), 9'[9H]xanthen]-3-one disodium salt (Cl 45380; Acid Red No. 87), 2',4',5',7'-tetrabromo-4,5,6,7-tetrachloro-3',6'-dihydroxyspiro[isobenzofuran-1(3H), 9'[9H]xanthen]-3-one disodium salt (Cl 45410; Acid Red No. 92), 3',6'-dihydroxy-4',5'-diiodospiro-[isobenzofuran-1(3H),9' (9H)-xanthen)-3-one disodium salt (Cl 45425; Acid Red No. 95), (2-sulfo-phenyl)di[4-(ethyl((4-sulfophenyl)-methyl)amino)phenyl]-carbenium disodium salt, betaine (Cl 42090; Acid Blue No. 9; FD&C Blue No. 1), 1,4-bis [(2-sulfo-4-methylphenyl)amino]-9,10-anthraquinone-disodium salt(Cl 61570; Acid Green No. 25), bis[4-(dimethylamino)-phenyl]-(3,7-disulfo-2-hydroxy-naphth-1-yl)-carbenium inner salt, monosodium salt (Cl 44090; Food Green No. 4; Acid Green No. 50), bis[4-(diethylamino)phenyl](2,4-disulfophenyl) -carbenium inner salt, sodium salt(2:1) (Cl 42045; Food Blue No. 3; Acid Blue No. 1), bis[4-(diethyl-amino)phenyl](5-hydroxy-2,4-disulfophenyl)carbenium inner salt, calcium salt (2:1) (Cl 42051; Acid Blue No. 3), 1-amino-4-(cyclohexyl-amino)-9,10-anthraquinone-2-sulfonic acid, sodium salt (Xl 62045; Acid Blue No. 62), 2-(1,3-dihydro-3-oxo-5-sulfo-2H-indol-2-yliden)-2,3-dihydro-3-oxo-1H -indol-5-sulfonic acid disodium salt (Cl 73015; Acid Blue No. 74), 9-(2-carboxyphenyl)-3-[(2-methyl-phenyl)-amino]-6-[(2-methyl-4-sulfophenyl)amino]-xanthylium inner salt, monosodium salt (Cl 45190; Acid Violet No. 9), 1-hydroxy-4-[(4-methyl-2-sulfophenyl) amino]-9,10-anthraquinone sodium salt (Cl 60730; D&C Violet t No. 2; Acid Violet No. 43), bis[3-nitro-4-[(4-phenylamino)-3-sulfophenylamino]-phenyl]-sulfone (Cl 10410; Acid Brown No. 13), 5-amino-4-hydroxy-6-[(4-nitrophenyl)azo]-3-(phenylazo)-2,7-napthalene disulfonic acid disodium salt (Cl 20470; Acid Black No. 1), 3-hydroxy-4-[(2-hydroxynaphth-1-yl)azo]-7-nitro-1-napthalene sulfonic acid chromium complex (3:2) (Cl 15711; Acid Black No. 52), 3-[(2,4-dimethyl-5-sulfophenyl)azo]-4-hydroxy-1-napthalene sulfonic acid disodium salt (Cl 14700; Food Red No. 1; Ponceau SX; FD&C Red No. 4), 4-(acetylamino)-5-hydroxy-6-[(7-sulfo-4-[(4-sulfophenyl)azo]naphth-1-yl)azo]-1,7-napthalene disulfonic acid tetrasodium salt (Cl 128440; Food Black No. 1) and 3-hydroxy-4-(3-methyl-5-oxo-1-phenyl-4,5-dihydro-1H-pyrazole-4-yl -azo)napthalene-1-sulfonic acid sodium salt chromium complex (Acid Red No. 195).

Suitable cationic dyestuffs include, for example, the following:

9-(dimethylamino)-benzo[a]phenoxazin-7-ium-chloride (Cl 51175; Basic Blue No. 6), di[4-(diethylamino)phenyl][4-(ethylamino)naphthyl]carbenium chloride (Cl 42595; Basic Blue No. 7), 3,7-di(dimethylamino)phenothiazin-5-ium chloride (Cl 52015; Basic Blue No. 9), di[4-(dimethylamino)phenyl][4-(phenylamino) -naphthyl]-carbenium chloride (Cl 44045; Basic Blue No. 26), 2-[(4-(ethyl(2-hydroxyethyl)-amino)phenyl)azo]-6-methoxy-3-methyl-benzothiazolium methyl sulfate (Cl 11154; Basic Blue No. 41), 8-amino-2-bromo-5-hydroxy-4-imino-6-[(3-(trimethyl-ammonio)phenyl)amino]-1(4H)-napthalenone chloride (Cl 56059; Basic Blue No. 99), bis[4-(dimethylamino)-phenyl] [4-(methylamino) phenyl]-carbenium chloride (Cl 42535; Basic Violet No. 1), tris(4-amino-3-methylphenyl)carbenium chloride (Cl 42520; Basic Violet No. 2), tris[4-(dimethylamino) phenyl]carbenium chloride (Cl 42555; Basic Violet No. 3), 2-[3,6-(diethylamino)dibenzopyranium-9-yl]-benzoic acid chloride (CI 45170; Basic Violet No. 10), di(4-aminophenyl)-(4-amino-3-methylphenyl)carbenium chloride (CI 42510; Basic Violet No. 14), 1,3-bis[(2,4-diamino-5-methylphenyl)azo]-3-methylbenzene (CI 21010; Basic Brown No. 4), 1-[(4-aminophenyl)azo]-7-(trimethylammonio)-2-naphthol chloride (CI 12250; Basic Brown No. 16), 1-[(4-amino-2-nitrophenyl)azo]-7-(trimethyl-ammonio)-2-naphthol chloride (CI 12251; Basic Brown No. 17), 1-[(4-amino-3-nitrophenyl)azo]-7-(trimethylammonio)-2-naphthol chloride (CI 12251; Basic Brown No. 17), 3,7-diamino-2,8-dimethyl-5-phenyl-phenazinium chloride (CI 50240; Basic Red No. 2), 1,4-dimethyl-5-[(4-(dimethylamino)phenyl)azo]-1,2,4-triazolium chloride (CI 11055; Basic Red No. 22), 2-hydroxy-1-[(2-methoxy-phenyl)azo]-7-(trimethylammonio)-napthalene chloride (CI 12245; Basic Red No. 76), 2-[2-((2,4-dimethoxyphenyl) -amino) ethenyl]-1,3,3-trimethyl-3H-indole-1-ium chloride (CI 48055; Basic Yellow No. 11), 3-methyl-1-phenyl-4-[(3-(trimethyl-ammonio)phenyl)-azo]pyrazole-5-one chloride (CI 12719; Basic Yellow No. 57) and bis[4-(diethylamino)phenyl]phenyl carbenium hydrogen sulfate (1:1) (CI 42040; Basic Green No. 1).

Suitable nonionic dyestuffs (especially for producing an improved color balance and for production of special nuances) include the following:

1-amino-2-[(2-hydroxyethyl)amino]-5-nitrobenzene (HC Yellow No. 5), 1-(2-hydroxyethoxy)-2-[(2-hydroxyethyl) amino]-5-nitrobenzene (HC Yellow No. 4), 1-[(2-hydroxyethyl)amino]-2-nitrobenzene (HC Yellow No. 2), 2-[(2-hydroxyethyl)-amino]-1-methoxy-5-nitrobenzene, 2-amino-3-nitrophenol, 1-(2-hydroxy-ethoxy)-3-methylamino-4-nitrobenzene, 2,3-(dihydroxypropoxy)-3-methylamino-4-nitro-benzene, 2-[(2-hydroxyethyl) amino]-5-nitrophenol (HC Yellow No. 11), 3-[(2-aminoethyl)amino]-1-methoxy-4-nitrobenzene-hydrochloride (HC Yellow no.9), 1-[(2-ureidoethyl) amino]-4-nitrobenzene, 4-[(2,3-dihydroxypropyl)amino]-3-nitro-1-trifluoromethylbenzene (HC Yellow No. 6), 1-chloro-2,4-bis-[(2-hydroxyethyl)-amino]-5-nitrobenzene (HC Yellow No. 10), 4-[(2-hydroxyethyl) amino]-3-nitro-1-methylbenzene, 1-chloro-4-[(2-hydroxyethyl)amino]-3-nitrobenzene (HC Yellow No. 12), 4-[(2-hydroxyethyl)amino-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitro-benzamide (HC Yellow No. 15), 1-amino-4-[(2-hydroxyethyl)amino-2-nitrobenzene (HC Red No. 7), 2-amino-4,6-dinitrophenol, 2-ethylamino-4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl) amino]-2-nitrobenzene, 4-amino-1-[(2-hydroxyethyl)-amino]-2-nitrobenzene (HC Red No. 3), 4-amino-3-nitrophenol, 4-[(2-hydroxyethyl)-amino]-3-nitrophenol, 1-[(2-aminoethyl)amino]-4-(2-hydroxy-ethoxy)-2-nitro-benzene (HC Orange No. 2), 4-(2,3-dihydroxy-propoxy)-1-[(2-hydroxyethyl)-amino]-2-nitrobenzene (HC Orange No. 3), 1-amino-5-chloro-4-[(2,3-dihydroxypropyl) amino]-2-nitrobenzene (HC Red No. 10), 5-chloro-1,4-[di(2,3-dihydroxypropyl)amino-2-nitrobenzene (HC Red No. 11), 2-[(2-hydroxy-ethyl)amino]-4,6-dinitrophenol, 4-ethylamino-3-nitrobenzoic acid, 2-[(4-amino-2-nitrophenyl)amino]benzoic acid, 2-chloro-6-methylamino-4-nitrophenol, 2-chloro-6-[(2-hydroxyethyl)amino]-4-nitrophenol, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoline, 7-amino-3,4-dihydro-6-nitro-2H-1,4-benzoxazine (HC Red No. 14), 1,4-bis[(2-hydroxyethyl) amino]-2-nitrobenzene, 1-(2-hydroxyethyl)amino-2-nitro-4-[di(2-hydroxyethyl)-amino]-benzene (HC Blue No. 2), 1-amino-3-methyl-4-[(2-hydroxy-ethyl)amino]-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl)amino]-2-nitrobenzene (HC Blue No. 11), 1-[(2,3-dihydroxypropyl) amino]-4-[methyl-(2-hydroxyethyl)-amino]-2-nitrobenzene (HC Blue No. 10), 1-[(2,3-dihydroxypropyl) amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl)amino]-2-nitrobenzene (HC Blue No. 6), 2-((4-amino-2-nitrophenyl)amino)-5-dimethyl-amino-benzoic acid (HC Blue No. 13), 1,4-di [(2,3-dihydroxypropyl)amino]-9,10-anthraquinone, 1-[(2-hydroxyethyl)amino]-4-methylamino-9,10-anthraquinone (CI 61505, disperse Blue No. 3), 2-[(2-aminoethyl)amino]-9,10-anthraquinone (HC Orange No. 5), 1-hydroxy-4-[(4-methyl-2-sulfophenyl)amino]-9,10-anthraquinone, 1-[(3-aminopropyl)amino]-4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (CI 62015, disperse Red No. 11, Solvent Violet No. 26), 1,4-dihydroxy-5,8-bis[(2-hydroxyethyl)amino]-9,10-anthraquinone (CI 62500, Disperse Blue No. 7, Solvent Blue No. 69), 1-[di(2-hydroxyethyl)amino]-3-methyl-4-[(4-nitrophenyl)azo]-benzene (CI 11210, disperse Red No. 17), 4-[(4-aminophenyl)azo]-1-[di(2-hydroxyethyl) amino]-3-methylbenzene (HC Yellow No. 7), 2,6-diamino-3-[(pyridine-3-yl)azo]pyridine, 2-((4-(acetylamino)phenyl)-azo)-4-methylphenol (CI 11855; Disperse Yellow No. 3).

From the group of direct-dyeing dyestuffs 2-amino-4,6-dinitrophenol, 2-ethylamino-4,6-dinitrophenol, 2-[(2-hydroxyethyl)amino]-4,6-dinitrophenol and dyestuffs of the general formula (II):

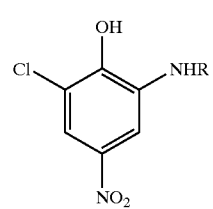

(II)

wherein R is hydrogen, methyl, ethyl or hydroxyethyl, are especially preferred.

The total concentration of direct-dyeing dyestuffs in the composition according to the invention amounts to about 0.1 to 10 percent by weight, preferably about 0.1 to 5 percent by weight.

Understandably the dyestuffs, in so far as they are bases, can also be used in the form of their physiologically compatible salts with organic or inorganic acids, for example hydrochloric acid or sulfuric acid, and/or, in so far as they have an aromatic OH group, in the form of their salts with bases, for example as alkali phenolates.

The above-described combinations of the compounds of formula (I) with oxidative hair dye pre-cursor compounds and/or direct dyeing dye compounds are applied for dyeing in a suitable dye carrier.

Furthermore additional conventional additive ingredients can be included in the compositions according to the invention. These additive ingredients can, for example, include antioxidants such as ascorbic acid, thioglycolic acid or sodium sulfite, as well as perfume oils, penetration agents, buffer systems, complex formers, preservatives, wetting agents, emulsifiers, thickeners and care materials.

The form of the dye composition according to the invention can be a solution, especially an aqueous or aqueous/alcoholic solution. However compositions according to the invention in the form of a creams, a gel or an emulsion are especially preferred. Their composition includes a mixture of dyestuff components with conventional cosmetic additive ingredients suitable for this sort of preparation.

Conventional additives for solutions, creams, emulsion or gels include, for example, solvents, such as water, lower aliphatic alcohols, for example, ethanol, propanol or isopropanol, glycerol or glycols, such as 1,2-propylene glycols; wetting agents or emulsifiers from the classes of anionic surfactants, cationic surfactants, amphoteric surfactants and nonionic surfactants, such as fatty alcohol sulfates, ethoxylated fatty alcohol sulfates, alkyl sulfonates, alkylbenzene sulfonates, ethoxylated nonylphenols, fatty acid alkanolamides and ethoxylated fatty acid esters; thickeners, such as higher fatty alcohols, starches, cellulose derivative compounds, petrolatum, paraffin oils and fatty acids, as well as care materials, such as cationic resins, lanolin derivative compounds, cholesterol, pantothenic acid and betaines. The above-mentioned ingredients are used in a common amount suitable for their purposes, for example the wetting agents and emulsifiers are used in a concentration of about 0.1 to 30 percent by weight, the thickeners in an amount of about 0.1 to 30 percent by weight the care materials in a concentration of about 0.1 to 5.0 percent by weight.

The ready-to-apply or ready-to-use hair dye mixture according to the invention is prepared by mixing the dye composition containing at least one compound of formula (I) together with an oxidizing agent just prior to use.

The oxidizing agent used for this type of dye composition is mainly hydrogen peroxide or its addition compounds with urea, melamine, sodium borate or sodium carbonate. Primarily an oxidizing composition is mixed with the dye composition, which is a 3 to 6 percent aqueous solution of hydrogen peroxide or its addition compounds. The weight ratio of the dye composition to the oxidizing composition in the mixture is preferably about 5:1 to 1:3, especially preferably from 1:1 to 1:2. Larger amounts of oxidizing agent, above all, are used when the dyestuff concentration in the hair dye composition is higher, or when a stronger bleaching of the hair is intended. It is also possible to use air oxygen for oxidation of the dyestuff instead of the above-described oxidizing composition.

The pH value of the ready-to-apply or ready-to-use hair dye mixture according to the invention is determined by the alkali content in the dye composition and the acid concentration in the oxidizing composition. The pH of the dye composition is from about 6 to about 11.5 and the pH of the oxidizing composition from about 2 to about 6.5. According to its composition the dye composition according to the invention can react like a weak acid, neutral composition or like an alkaline composition. The pH of the ready-to-apply or ready-to-use hair dye mixture is then from about 3 to 11, preferably from 5 to 10. The basic pH adjustment occurs preferably with ammonia, however also with organic amines, for example 2-amino-2-methyl-1-propanol, tris(hydroxymethyl)aminomethane, monoethanolamie and triethanolamine or also inorganic bases, such as sodium hydroxide and potassium hydroxide. Inorganic or organic acids, such as phosphoric acid, acetic acid, lactic acid, ascorbic acid, citric acid or tartaric acid, can be used to adjust the pH in the acid range.

Subsequently when dyeing hair with the ready-to-apply or ready-to-use hair dye mixture according to the invention it is applied to the hair in an amount sufficient for the dyeing of the hair, according to the abundance of the hair, usually about 60 to 200 grams. Then the mixture is allowed to act on the hair for a sufficient time interval at about 15° C. to 50° C., preferably at about 30° C. to 40° C., for about 10 to 45 minutes, preferably about 30 minutes. Subsequently the mixture is rinsed from the hair and dried. The hair is optionally washed with a shampoo, if necessary, and optionally after-rinsed with a weak organic acid, for example citric or tartaric acid. Then the hair is dried.

The dye compositions according to the invention containing the 4,5-diaminopyrazoles of formula (I) provide hair dyeing with outstanding color fastness, especially light fastness, wash fastness and rubbing fastness. In regard to their color-imparting properties the hair dye compositions according to the invention provide a broad palette of different color shades, especially in the fashionable red range, according to the type and amounts of the various dye compound ingredients. A special color intensity and brightness characterize the color shades produced according to the invention. Very good color properties are provided by the dye composition according to the present invention. Particularly the hair dye composition also provides uniform and maintainable good dyeing on pre-damaged hair, which has been damaged to various different extents.

The following examples illustrate the above-described invention in more detail, but the details in these examples should not be considered as limiting the claims appended hereinbelow.

EXAMPLES

Example 1

Preparation of 1,2-bis-(4,5-diaminopyrazol-1-yl)ethane tetrahydrochloride

Step 1.1: Glyoxal-bis-(2-(2-cyanoethyl))hydrazone

To 170.2 g of 2-cyanoethylhydrazine 145.1 g of 40% glyoxal are added drop-wise with mild cooling so that a temperature of 40° C. is not exceeded. Subsequently the reaction mixture is stirred further for about 1 hour at room temperature, whereby the hydrazone crystallizes out. The product is filtered with suction, pressed sufficiently and dried.

| | |
|---|---|
| Yield: | 170.5 g beige crystals |
| Melting Point: | 96 to 97° C. |
| $^1$H-NMR (DMSO-$d_6$): | $\delta$ = 2.66 ppm(t, $^3J_{HH}$ = 10.75 Hz, 2H); 3.29 ppm(dt, $^3J_{HH}$ = 10.75 Hz, $^3J_{HH}$ = 8 Hz, 2H); 7.32 ppm(s, 2H); 7.33 ppm(t, $^3J_{HH}$ = 8 Hz, 2H). |

Step 1.2: 1,2-bis-(5-aminopyrazol-1-yl)ethane 17.3 g of hydrazone from step 1.1 are heated in 150 ml butoxyethanol together with 10.1 g of potassium-tertbutylate at 110° C. After one hour the reaction mixture is cooled and filtered with suction to obtain the precipitated crystals. After washing with a little butoxyethanol and drying 18.2 g of copper colored flakes with a metallic luster are obtained.

| Melting Point: | 208 to 209° C. |
|---|---|
| $^1$H-NMR (DMSO-d$_6$): | δ = 4.17 ppm(s, 4H); 5.06 ppm(s, 4H); 7.27 ppm(d, $^3$J$_{HH}$ = 3 Hz, 2H); 7.10 ppm (d, $^3$J$_{HH}$ = 3 Hz, 2H). |

Step 1.3: 1,2-bis-(5-amino-4-nitrosopyrazol-1-yl) ethane•2HCl 10 g of 1,2-bis-(5-aminopyrazol-1-yl) ethane from step 1.2 are mixed with 29.6 g of concentrated hydrochloric acid in 150 ml of tetrahydrofuran with cooling to 0 to 5° C. 12.2 g of isopentyl nitrite are added drop-wise within 30 minutes to the resulting reaction mixture, which is then stirred for three hours. The yellow suspension is filtered under vacuum and the final product is thus obtained without further purification.

Step 1.4: 1,2-bis-(4,5-diaminopyrazol-1-yl) ethane•4HCl

The crude product from step 1.3 in 150 ml water is hydrogenated with 1.5 g palladium (10% activated carbon) under a slightly elevated hydrogen pressure. After six hours the catalyst is filtered off and the filtrate concentrated under reduced pressure to about 50 ml. After the addition of 100 ml concentrated hydrochloric acid the mixture is stirred for 30 minutes in an ice bath, the residue is filtered with suction and dried under vacuum.

| Yield: | 11.1 g of a beige product |
|---|---|
| Melting Point: | >250° C. |
| $^1$H-NMR (DMSO-d$_6$): | δ = 4.27 ppm(s, 4H); 6.80 ppm(s, broad, 8H); 7.32 ppm(s, 2H); 9.95 ppm(s, broad, 4H). |
| FAB-MS: | 223 [M + H]$^+$ |

(FAB-MS means fast atom bombardment mass spectroscopy)

Example 2

Preparation of 1,2-bis-(4,5-diaminopyrazol-1-yl) ethane Sulfate 3.23 g of 1,2-bis-(5-amino-4-nitrosopyrazol-1-yl)ethane dihydrochloride from Example 1, step 1.3, are neutralized in 50 ml water with an ammonia solution. The precipitate obtained is filtered with suction and hydrogenated in 30 ml of 2-methoxyethanol under a slight excess hydrogen pressure on 0.2 g of palladium (10% activated carbon). After 6 hours the catalyst is filtered off, the filtrate is cooled in an ice bath and stirred while one gram of concentrated sulfuric acid is added drop-wise. The precipitated product is filtered with suction and re-crystallized from 30 ml ethanol/water 1:1. A beige product is obtained after filtering and drying in vacuum in an amount of 1.7 g.

Melting Point: >250° C.

Elemental analysis: (C$_8$H$_{14}$N$_8$×H$_2$SO$_4$; M=320.33)

Accounting for the presence of 1.44% crystallization water the following values result:

|  | % C | % H | % N | % S |
|---|---|---|---|---|
| Calc.: | 29.56 | 5.12 | 34.48 | 9.87 |
| Found: | 29.40 | 4.90 | 33.60 | 9.90 |

Example 3

1,4-bis-(4,5-diaminopyrazol-1-yl-methyl)benzene•4HCl

Step 3.1: 3-(N'-{4-[(2-cyanoethyl)hydrazonomethyl]benzyliden}-hydrazino)propionitrile To a suspension of 102 g terephthaldehyde in 700 ml methanol 129.4 g of 2-cyanoethylhydrazine are added drop-wise within 20 minutes. The temperature increases to about 50° C., and an orange-red solution generally arises. After about 10 minutes further crystallization occurs. Stirring continues for 30 minutes and a precipitate that appears is filtered with suction. After washing with a little cold methanol the precipitate is dried under vacuum. 187 g of beige colored product are produced.

Melting Point: 111 to 113° C.

Elemental analysis: (C$_{14}$H$_{16}$N$_6$; M=268.32)

|  | % C | % H | % N |
|---|---|---|---|
| Calc.: | 62.67 | 6.01 | 31.32 |
| Found: | 62.40 | 6.08 | 31.48 |

Step 3.2 1,4-bis-(5-diaminopyrazol-1-yl-methyl)benzene

The 3-(N'-{4-[(2-cyanoethyl)hydrazonomethyl]-benzyliden}-hydrazino)propionitrile obtained in step 3.1 is heated in 750 ml butanol/45 g potassium tert-butylate at 75° C. After 2 hours the reaction mixture is cooled to room temperature and filtered to obtain a precipitate. After washing the precipitate with a little cold butanol and drying it under vacuum 91.1 g of bright brown product are obtained.

Melting Point: 204 to 206° C.

$^1$H-NMR (DMSO-d$_6$): δ=5.07 ppm (s, 4H); 5.21 ppm (s, 4H); 5.29 ppm (d, $^3$J$_{HH}$=3.1 Hz, 2H); 7.06 ppm (d, $^3$J$_{HH}$=3.1 Hz, 2H); 7.07 ppm (s, 4H).

Elemental analysis: (C$_{14}$H$_{16}$N$_6$; M=268.32)

|  | % C | % H | % N |
|---|---|---|---|
| Calc.: | 62.67 | 6.01 | 31.32 |
| Found: | 62.61 | 6.13 | 31.49 |

Step 3.3 1,4-bis-(5-amino-4-nitrosopyrazol-1-yl-methyl)benzene•2HCl 2.2 g of 1,4-bis-(5-aminopyrazol-1-yl-methyl)benzene from step 3.2 are suspended in 40 ml ethanol, mixed with 1.9 g of concentrated hydrochloric acid and subsequently mixed drop-wise with 2.2 g of isoamyl nitrite in an ice bath within 15 minutes. After another three hours of stirring in the ice bath the reaction mixture is filtered with suction and dried.

2.7 g of a reddish solid is obtained, which is further processed as a crude product.

Step 3.4 1,4-bis-(4,5-diaminopyrazol-1-yl-methyl)benzene•4HCl 2.7 g of the 1,4-bis-(5-amino-4-nitrosopyrazol-1-yl-methyl)benzene dihydrochloride from step 3.3 are hydrogenated in 40 ml ethanol with 0.3 g palladium (10% activated carbon) under a slightly elevated hydrogen pressure. After five hours the catalyst is filtered off. 20 ml ethanolic hydrochloric acid are added to the filtrate with stirring for 30 minutes, the filtrate is filtered and dried in vacuum.

Yield: 2.5 g of a beige product. The titration with 0.1 N sodium hydroxide established that the product is the tetrachloride.

$^1$H-NMR (DMSO-$d_6$): δ5.15 ppm (s, 4H); 5.7 ppm (s, broad, NH and water); 7.14 ppm (s, 4H); 7.29 ppm (s, 2H); 9.90 ppm (s broad, 4H). FAB-MS: 299 [M+H]$^+$

Example 4

1,3-bis-(4,5-diaminopyrazol-1-yl-methyl)benzene•4HCl

Step 4.1: 1,3-bis-(3,5-dibromo-4-nitropyrazol-1-yl-methyl)benzene 13.54 g of 3,5-dibromo-4-nitropyrazole, 11.1 g potassium carbonate, 0.8 g of potassium iodide and 6.6 g α,α'-dibromo-m-xylene are heated to 100° C. in 40 ml of dimethyl formamide. After 50 minutes the reaction mixture is allowed to cool and poured into 400 ml water. The precipitate is filtered, washed with water and dried in vacuum.

Yield: 13.9 g of yellow product.

$^1$H-NMR (DMSO-$d_6$): δ=5.53 ppm (s, 4H); 7.03 ppm (s, 1H); 7.24 ppm (d, $^3J_{HH}$=12.85 Hz, 2H); 7.43 ppm (t, $^3J_{HH}$=12.85 Hz, 1H).

Step 4.2: 1,3-bis-(5-benzylamino-3-bromo-4-nitropyrazol-1-yl-methyl)-benzene 13.9 g of 1,3-bis-(3,5-dibromo-4-nitropyrazol-1-yl-methyl)benzene from step 4.1 are heated together with 6.5 g of benzylamine in 130 ml of n-propanol for 2 hours at 95° C. Subsequently the reaction mixture is cooled and poured into 400 ml water. The precipitate is filtered with suction and recyrstallized from 150 ml of acetonitrile.

Yield: 6.6 g $^1$H-NMR (DMSO-$d_6$): δ=4.51 ppm (d, $^3J_{HH}$=11 Hz, 4H); 5.22 ppm (s, 4H); 6.75 ppm (s, 1H); 7.04 ppm (d, $^3J_{HH}$=11 Hz, 2H); 7.16 ppm (d, $^3J_{HH}$=11 Hz, 2H); 7.2–7.4 ppm (m, 6H); 8.01 ppm (t, $^3J_{HH}$=11 Hz, 2H).

Step 4.3: 1,3-bis-(4,5-diaminopyrazol-1-yl-methyl)-benzene•4HCl 1.7 g of 1,3-bis-(5-benzylamino-3-bromo-4-nitropyrazol-1-yl-methyl)benzene from step 4.2 in 30 ml 2-methoxyethanol are hydrogenated for 3 hours at 50° C. with 0.2 g of palladium (10% activated carbon) and 5 bar hydrogen. Subsequently the reaction mixture is cooled, filtered and evaporated to dryness. The residue is taken up in 20 ml of ethanolic hydrochloric acid so that crystallization occurred. The resulting mixture is filtered to obtain the crystalline precipitate, which is dried in vaccuum to obtain 1.5 g of a beige product. Titration with 0.1 N sodium hydroxide established that the product is the tetrahydrochloride.

FAB-MS: 299 [M+H]$^+$

Example 5

Preparation of 1,3-bis-(4,5-diaminopyrazol-1-yl)propane•4HCl

Step 5.1: 1,3-bis-(3,5-dibromo-4-nitro-pyrazol-1-yl)propane

In 60 ml dimethylformamide 27.01 g of 3,5-dibromo-4-nitropyrazole, 16.4 g of sodium acetate and 11 g of 1,3-dibromopropane are heated at 100° C. The reaction mixture is cooled after two hours and poured with stirring into 500 ml of ice water. The precipitated product is filtered with suction, washed thoroughly with water and dried in vacuum at 60° C.

Yield: 25.6 g of beige product Melting Point: 194 to 198° C.

Elemental analysis: ($C_9H_6Br_4N_6O_4$; M=581.82)

|  | % C | % H | % N |
|---|---|---|---|
| Calc.: | 18.58 | 1.04 | 14.44 |
| Found: | 18.43 | 1.05 | 14.20 |

Step 5.2: 1,3-bis-(5-benzylamino-3-bromo-4-nitropyrazol-1-yl)-propane 11.6 g of 1,3-bis-(3,5-dibromo-4-nitropyrazol-1-yl)propane from step 5.1 are heated together with 6.5 g of benzylamine in 180 ml of n-propanol for 1 hour at 100° C. Subsequently the reaction mixture is cooled and poured into 1000 ml water. The precipitate is filtered with suction, washed with water and dried in vacuum at 60° C.

Yield: 10.9 g yellow product Melting Point: 148 to 151° C.

Elemental analysis: ($C_{23}H_{22}Br_2N_8O_4$; M=634.30)

|  | % C | % H | % N |
|---|---|---|---|
| Calc.: | 43.55 | 3.50 | 17.67 |
| Found: | 43.85 | 3.54 | 17.38 |

Step 5.3: 1,3-bis-(4,5-diaminopyrazol-1-yl)-propane•4HCl 3.1 g of 1,3-bis-(5-benzylamino-3-bromo-4-nitropyrazol-1-yl)propane from step 5.2 in 80 ml 2-methoxyethanol are hydrogenated for 6 hours at room temperature with 0.4 g of palladium (10% activated carbon) and 5 bar hydrogen. Subsequently the reaction mixture is filtered and evaporated nearly to dryness. The residue is taken up in 20 ml of ethanol and 20 ml of 2 N hydrochloric acid with stirring so that crystallization occurred. The resulting mixture is filtered to obtain the crystalline precipitate, which is dried in vacuum to obtain 0.2 g of a beige product. Titration with 0.1 N sodium hydroxide established that the product is the tetrahydrochloride.

$^1$H-NMR (DMSO-$d_6$): δ=2.05 ppm (t broadened, $^3J_{HH}$=11 Hz, 2H); 3.96 ppm (t, $^3J_{HH}$=11 Hz, 4H); 4.01 ppm (s, broad, NH and water); 7.28 ppm (s, 2H); 9.82 ppm (s broad, 4H).
FAB-MS: 237 [M+H]$^+$

Example 6

1,3-bis-(4,5-diamino-3-phenylpyrazol-1-yl)
propane•4HCl

Step 6.1: 1,3-bis-(5-benzylamino-4-nitro-3-phenyl-
pyrazol-1-yl)propane 3.7 g of 1,3-bis-(5-benzylamino-3-bromo-4-nitropyrazol-1-yl)propane from step 5.2 in 40 ml 1,2-dimethoxyethane are mixed under nitrogen with 3.8 g phenyl boric acid, 1.2 g of tetrakis(triphenylphosphin)palladium (0) and a solution of 8.3 g of potassium carbonate in 30 ml water. The resulting reaction mixture is subsequently heated under reflux under nitrogen. After five hours the reaction mixture is heated over silica gel (hyflo super-gel of Celite Co.), filtered and the filtrate cooled in an ice bath. The precipitate coming down is filtered, washed with water and recrystallized from 50 ml ethanol. After drying in vacuum at 60° C. one obtains 1.5 g of a yellow product.

Melting point: 142 to 144° C.

$^1$H-NMR (DMSO-d$_6$): δ=2.35 ppm (t broadened, $^3J_{HH}$=11 Hz, 2H); 4.22 ppm (t, $^3J_{HH}$=11 Hz, 4H); 4.74 ppm (d, $^3J_{HH}$=11 Hz, 4H); 7.1 to 7.4 ppm (m, 20H); 7.70 ppm (d, $^3J_{HH}$=11 Hz, 2H).

Step 6.2: 1,3-bis-(4,5-dibromo-4-nitro-3-phenyl-
pyrazol-1-yl)propane•4HCl 1.5 g 1,3-bis-(5-benzylamino-4-nitro-3-phenylpyrazol-1-yl)propane in 50 ml acetic acid from step 6.1 are hydrogenated for 15 hours with 1.5 g of palladium (10% activated carbon) and 5 bar hydrogen. Subsequently the reaction mixture is filtered and evaporated to dryness. The residue is taken up in 20 ml of ethanol and 10 ml of 2 N hydrochloric acid and heated under reflux conditions for three hours. A viscous precipitate appeared after cooling in an ice bath. The supernatant solution is decanted and taken up in 20 ml of ethanolic hydrochloric acid. 0.5 g of beige product resulted.

$^1$H-NMR (DMSO-d$_6$): δ=2.18 ppm (t broadened, $^3J_{HH}$=11 Hz, 2H); 3.50 ppm (s, broad, NH and water); 4.02 (t, $^3J_{HH}$=11 Hz, 4H); 7.2 to 7.7 ppm (m, 10H); 10.10 ppm (s broad, 4H).

FAB-MS: 389 [M+H]$^+$

Example 7

Basic Oxidation Hair Dye Composition

| | |
|---|---|
| 0.30 g | ascorbic acid |
| 0.40 g | sodium sulfite |
| 10.00 g | sodium lauryl ether sulfate, 28% aqueous solution |
| 7.85 g | ethanol |
| 0.92 g | pyrazole of formula (I) according to example 1 |
| y g | coupler according to table I |
| 9.10 g | ammonia, 25% aqueous solution |
| to 100.0 g | water, demineralized. |

Immediately prior to application 100 grams of each of the above-described dye compositions are mixed with 100 grams of a 6% aqueous hydrogen peroxide solution. The obtained ready-to-apply dye solutions are applied to bleached hair in the required amount to dye the hair. After an acting time of 30 minutes at 40° C. the hair is washed with a shampoo, rinsed with water and dried. The resulting colors and intensities for the dyed hair are tabulated in Table I.

TABLE I

HAIR COLORS AND INTENSITIES OBTAINED WITH HAIR DYE
COMPOSITIONS ACCORDING TO THE EXAMPLE 7

| Example | Coupler, grams | Shade | Color Intensity |
|---|---|---|---|
| 7.1 | 0.28 g resorcinol | Rosé | O |
| 7.2 | 0.31 g 1,3-dihydroxy-2-methylbenzene | Rosé | O |
| 7.3 | 0.35 g 1,3-dihydroxy-2,4-dimethylbenzene | Red-blond | + |
| 7.4 | 0.27 g 3-aminophenol | Copper-gold | ++ |
| 7.5 | 0.31 g 5-amino-2-methyphenol | Orange-red | ++ |
| 7.6 | 0.64 g 5-((2-hydroxyethyl)-amino)-2-methoxyaniline dihydrochloride | Black-violet | ++ |
| 7.7 | 0.56 g 6-amino-3,4-dihydro-2H-1,4-benzoxazine dihydrochloride | Red-violet | ++ |
| 7.8 | 0.52 g 3,4-dihydro-6-hydroxy-1,4(2H)-benzoxazine sulfate(2:1)hydrate(2:1) | Ash-blond | ++ |
| 7.9 | 0.59 1,3-diamino-4-methoxy-benzene sulfate | Wine-red | ++ |
| 7.10 | 0.60 1,3-diamino-4-(2-hydroxy-ethoxy)-benzene dihydrochloride | Dark violet | ++ |
| 7.11 | 1.08 g 1,3-di(2,4-diaminophenoxy)propane tetrahydrochloride | Dark wine-Red | ++ |
| 7.12 | 0.36 g 1-chloro-2,4-dihydroxybenzene | Raspberry | ++ |
| 7.13 | 0.57 g 3-amino-6-methoxy-2-(methylamino)-pyridine hydrochloride | Blue-violet | ++ |
| 7.14 | 0.35 g 5-hydroxy-1,3-benzodioxole | Cognac | + |
| 7.15 | 0.43 g 5-amino-1,3-benzodioxole hydrochloride | Raspberry | + |
| 7.16 | 0.54 g 5-((2-hydroxyethyl)-amino)-1,3-benzodioxole hydrochloride | Chimney-red | ++ |
| 7.17 | 0.36 g 1-naphthol | Violet | ++ |
| 7.18 | 0.44 g 4-methoxy-1-naphthol | Violet | + |
| 7.19 | 0.50 g 1-acetoxy-2-methylnaphthol | Red-violet | ++ |

TABLE I-continued

HAIR COLORS AND INTENSITIES OBTAINED WITH HAIR DYE COMPOSITIONS ACCORDING TO THE EXAMPLE 7

| Example | Coupler, grams | Shade | Color Intensity |
|---|---|---|---|
| 7.20 | 0.61 g 3,5-diamino-2,6-dimethoxypyridine dihydrochloride | Wine-red | ++ |
| 7.21 | 0.40 g 1,7-dihydroxynaphthalene | Violet | + |
| 7.22 | 0.45 g 3-dimethylaminophenyl urea | Steel-blue | ++ |
| 7.23 | 0.33 g 4-hydroxyindole | Red-violet | ++ |
| 7.24 | 0.39 g 3-amino-2-chloro-6-methylphenol | Copper-red | ++ |
| 7.25 | 0.56 g 2-chloro-5-((2,2,2-trifluoroethyl)amino)-phenol | Wine-red | ++ |
| 7.26 | 0.45 g 3-amino-2,4-dichlorophenol | Bordeaux | ++ |
| 7.27 | 0.36 g 5-amino-2-chlorophenol | Glowing Red | ++ |

(O) = medium;
(+) = strong;
(++) = very strong

Example 8

Basic Oxidation Hair Dye Composition

| | |
|---|---|
| 0.30 g | ascorbic acid |
| 0.40 g | sodium sulfite |
| 10.00 g | sodium lauryl ether sulfate, 28% aqueous solution |
| 7.85 g | ethanol |
| 1.11 g | pyrazole of formula (I) according to example 3 |
| y g | coupler according to table II |
| 9.10 g | ammonia, 25% aqueous solution |
| to 100.0 g | water, demineralized. |

Immediately prior to application 100 grams of each of the above-described dye compositions are mixed with 100 grams of a 6% aqueous hydrogen peroxide solution. The ready-to-apply dye solutions are applied to bleached hair samples in the required amount to dye the hair. After an acting time of 30 minutes at 40° C. the hair is washed with a shampoo, rinsed with water and dried. The resulting colors and intensities of the dyed hair are tabulated in Table II.

TABLE II

HAIR COLORS AND INTENSITIES OBTAINED WITH HAIR DYE COMPOSITIONS ACCORDING TO EXAMPLE 8

| Example | Coupler, grams | Color Shade | Intensity |
|---|---|---|---|
| 8.1 | 0.56 g resorcinol | Raspberry | + |
| 8.2 | 0.54 g 3-aminophenol | Wine-red | ++ |
| 8.3 | 0.62 g 5-amino-2-methylphenol | Copper-Red | ++ |
| 8.4 | 1.28 g 5-((2-hydroxyethyl)amino)-2-methoxyaniline dihydrochloride | Black, Violet Reflex | ++ |
| 8.5 | 1.20 g 1,3-diamino-4-(2-hydroxyethoxy)-benzene dihydrochloride | Red-black | ++ |
| 8.6 | 2.16 g 1,3-di(2,4-diaminophenoxy) propane tetrahydrochloride | Black, Red Reflex | ++ |
| 8.7 | 0.90 g N-(3-dimethylamino-phenyl)-urea | Dark blue | ++ |

(O) = medium;
(+) = strong;
(++) = very strong

Examples 9–11

Basic Creamy Oxidation Hair Dye Composition

| | |
|---|---|
| 15.00 g | cetyl stearyl alcohol (50/50) |
| 5.00 g | glyceryl monostearate |
| 2.00 g | cocamide DEA |
| 10.00 g | sodium lauryl ether sulfate, 28% aqueous solution |
| 0.30 g | ascorbic acid |
| 0.40 g | sodium sulfite |
| x g | dyestuff according to Table III |
| 4.50 g | ammonia, 25% aqueous solution |
| to 100.0 g | water, demineralized. |

The pH of the cream is between 10.1 and 10.5.

Immediately prior to application 100 grams of each of the above-described dye compositions are mixed with 100 grams of a 6% aqueous hydrogen peroxide solution. The obtained ready-to-apply dye solutions are applied to bleached hair samples in the required amount to dye the hair. After an acting time of 30 minutes at 40° C. the hair samples are washed with a shampoo, rinsed with water and dried. The resulting compositions and colors of the dyed hair samples are tabulated in Table III.

TABLE III

THREE DYE COMPOSITIONS ACCORDING TO EXAMPLES 9 to 11 AND HAIR COLORS OBTAINED BY DYEING HAIR WITH THEM

| DYESTUFF | 9 | 10 | 11 |
|---|---|---|---|
| Pyrazole according to Ex. 2 | 4.26 g | | |
| Pyrazole according to Ex. 4 | | | 4.26 g |
| Pyrazole according to Ex. 5 | | 2.22 g | |
| 3-aminophenol | | | 0.22 g |
| 4-amino-3-methylphenol | 0.01 g | | 0.10 g |
| 5-amino-2-methyl-phenol | 0.39 g | | |
| 3-amino-2-chloro-6-methylphenol | 1.01 g | | 0.30 g |
| 1,3-dihydroxybenzene | | 0.56 g | |
| 2-amino-6-chloro-4-nitrophenol.HCl | | 0.51 g | |
| 2-chloro-6-(ethylamino)-4-nitrophenol | | 0.05 g | |
| 1,4-diamino-2-methyl-benzene sulfate | | | 0.31 g |
| 1,4-diamino-2-(2-hydroxy-ethyl)-benzene sulfate | | | 0.20 g |

TABLE III-continued

THREE DYE COMPOSITIONS ACCORDING TO EXAMPLES 9 to 11 AND HAIR COLORS OBTAINED BY DYEING HAIR WITH THEM

| DYESTUFF | 9 | 10 | 11 |
|---|---|---|---|
| N-(3-dimethylaminophenyl)-urea | | | 0.34 g |
| Hair Color obtained | Glowing Bright Red | Bright Red-gold | Black with red-violet reflex |

Example 12

Gel-form Oxidation Hair Dye Composition

| | |
|---|---|
| 15.00 g | oleic acid |
| 3.00 g | glycerol |
| 7.00 g | isopropanol |
| 0.50 g | ascorbic acid |
| 0.40 g | sodium sulfite |
| 0.40 g | sodium hydroxide |
| 10.00 g | ammonia, 25% aqueous solution |
| 1.00 g | pyrazole according to example 2 |
| 0.31 g | 1,4-diamino-2-methylbenzene sulfate |
| 0.20 g | 1,4-diamino-2-(2-hydroxyethyl)benzene sulfate |
| 0.10 g | 4-amino-3-methylphenol |
| 0.46 g | 1,3-diamino-4-(2-hydroxyethoxy)benzene dihydrochloride |
| 0.24 g | 5-amino-2-methylphenol |
| 0.21 g | 3-aminophenol |
| to 100.0 g | water, demineralized. |

The gel had a pH of 10.8.

Immediately prior to application 100 grams of the above-described dye composition are mixed with 100 grams of a 6% aqueous hydrogen peroxide solution. The obtained ready-to-apply dye solution is applied to 50% gray hair in the required amount to dye the hair. After an acting time of 30 minutes at 40° C. the hair is washed with a shampoo, rinsed with water and dried. The hair is dyed black with an aubergine reflex.

Example 13

Acidic Creamy Oxidation Hair Dye Composition

| | |
|---|---|
| 15.00 g | cetyl stearyl alcohol (50/50) |
| 5.00 g | glyceryl monostearate |
| 2.00 g | cocamide DEA |
| 10.00 g | sodium lauryl ether sulfate, 28% aqueous solution |
| 0.30 g | ascorbic acid |
| 0.40 g | sodium sulfite |
| 0.56 g | pyrazole according to example 3 |
| 0.67 g | pyrazole according to example 6 |
| 0.25 g | 5-((2-hydroxyethyl)amino-1,3-benzodioxole hydrochloride |
| 0.18 g | 3-amino-2-chloro-6-methylphenol |
| 0.22 g | 6-amino-3,4-dihydro-2H-1,4-benzoxazine dihydrochloride |
| to 100.0 g | water, demineralized. |

The pH of the cream is adjusted with ammonia, 25%, to pH=6.6.

Immediately prior to application 100 grams of the above-described dye carrier composition are mixed with 100 grams of a 6% aqueous hydrogen peroxide solution. The obtained ready-to-apply dye solution is applied to various different hair samples (see table IV) in the required amount to dye the hair. After an acting time of 30 minutes at 40° C. the hair is washed with a shampoo, rinsed with water and dried. The resulting colors of the dyed hair are tabulated in Table IV.

TABLE IV

COLORS OF DIFFERENT HAIR SAMPLES DYED WITH A COMPOSITION ACCORDING TO THE INVENTION

| UNDYED HAIR SAMPLES | DYED COLOR |
|---|---|
| White YAK HAIR | AUBERGINE |
| HUMAN HAIR, up to 50% Gray | AUBERGINE, Gray portion completely covered |
| HUMAN HAIR, medium brown | dark AUBERGINE |

Example 14

Comparative Example: Comparative Test of Color Stability

Dye Carrier Composition

| | |
|---|---|
| 0.30 g | ascorbic acid |
| 0.40 g | sodium sulfite |
| 10.00 g | sodium lauryl ether sulfate, 28% aqueous solution |
| 7.85 g | ethanol |
| X | pyrazole of formula (I) according to tables V to VIII |
| 0.31 g | 5-amino-2-methylphenol |
| 9.10 g | ammonia, 25% aqueous solution |
| to 100.0 g | water, demineralized. |

Immediately prior to application 100 grams of each of the above-described dye carrier composition are mixed with 100 grams of a 6% aqueous hydrogen peroxide solution. The obtained ready-to-apply dye solutions are applied to hair samples described hereinbelow in the required amount to dye the hair. After an acting time of 30 minutes at 40° C. the hair is washed with a shampoo, rinsed with water and dried. After that the L*a*b*-values of the reference or control samples are measured. Subsequently the samples are shampooed for one minute, three times each, dried and the L*a*b*-values are again measured. The results of these comparative experiments are summarized in Table V to VIII.

The results of dyeing the following different hair samples with these dye compositions are described hereinbelow.

a) Human hair, medium blond

This human hair is not previously dyed, bleached or waved.

b) Human hair, bleached

This medium blond human hair is treated for 15 minutes at 40° C. with a commercial bleaching agent, rinsed with water and then dried.

c) Human hair, permanent waved.

This medium blond human hair is treated for 20 minutes at 40° C. with a commercial permanent wave composition, then fixed, post-treated with a conventional hair care rinse agent, rinsed with water and then dried.

The ΔE values for color changes in L*a*b*-System are calculated with the following equation $$\Delta E = \{(L_i - L_o)^2 + (a_i - a_o)^2 + (b_i - b_o)^2\}^{1/2}$$

wherein $L_o$, $a_o$ and $b_o$ are the measured values prior to washing and $L_i$, $a_i$ and $b_i$ are the measured values after washing. As a partial explanation, the higher the ΔE value, the higher is the color loss and/or color shade change.

The ΔE values are tabulated in Tables V to VII. The calculation of the average values occurred by means of Microsoft Excel 97 SR-2, function "average value".

TABLE V

COMPOSITIONS ACCORDING TO THE INVENTION; with x = 0.92 g PYRAZOLE OF EXAMPLE 1

| HAIR TYPE | | L* | a* | b* | ΔE |
|---|---|---|---|---|---|
| (a) untreated | dyed: | 31.81 | 20.69 | 20.18 | |
| Human hair | washed: | 32.63 | 20.94 | 20.92 | 1.13 |
| (b) bleached | dyed: | 36.97 | 34.53 | 30.90 | |
| Human hair | washed: | 38.41 | 34.23 | 31.72 | 1.68 |
| (c) permanent waved | dyed: | 26.72 | 20.70 | 16.39 | |
| Human hair | washed: | 27.09 | 21.57 | 15.43 | 1.35 |
| | | | Average value of ΔE = | | 1.39 |

TABLE VI

COMPOSITIONS ACCORDING TO THE PRIOR ART; with x = 0.46 g 4,5-DIAMINO-1-METHYLPYRAZOLE of EP-OS 0 375 977

| HAIR TYPE | | L* | a* | b* | ΔE |
|---|---|---|---|---|---|
| (a) untreated | dyed: | 34.73 | 19.64 | 24.15 | |
| Human hair | washed: | 37.73 | 19.16 | 25.68 | 3.40 |
| (b) bleached | dyed: | 47.49 | 35.19 | 41.24 | |
| Human hair | washed: | 51.97 | 32.22 | 40.77 | 5.40 |
| (c) permanent waved | dyed: | 33.10 | 18.20 | 22.61 | |
| Human hair | washed: | 37.04 | 16.64 | 22.72 | 4.24 |
| | | | Average value of ΔE = | | 4.35 |

TABLE VII

COMPOSITIONS ACCORDING TO THE PRIOR ART; with x = 0.57 g 4,5-DIAMINO-3-METHYL-1-(2-HYDROXYETHYL)PYRAZOLE of EP-OS 0 740 931

| HAIR TYPE | | L* | a* | b* | ΔE |
|---|---|---|---|---|---|
| (a) untreated | dyed: | 26.59 | 21.78 | 9.72 | |
| Human hair | washed: | 29.98 | 21.74 | 11.05 | 3.64 |
| (b) bleached | dyed: | 31.05 | 34.56 | 10.86 | |
| Human hair | washed: | 37.78 | 33.26 | 13.74 | 7.43 |
| (c) permanent waved | dyed: | 23.41 | 22.10 | 8.52 | |
| Human hair | washed: | 30.37 | 20.76 | 12.49 | 8.12 |
| | | | Average value of ΔE = | | 6.40 |

TABLE VIII

COMPOSITIONS ACCORDING TO THE PRIOR ART; with x = 0.53 4,5-DIAMINO-1-ISOPROPYLPYRAZOLE of DE-OS 42 34 885

| HAIR TYPE | | L* | a* | b* | ΔE |
|---|---|---|---|---|---|
| (a) untreated | dyed: | 32.57 | 28.71 | 20.52 | |
| Human hair | washed: | 33.76 | 28.59 | 21.08 | 1.32 |
| (b) bleached | dyed: | 36.63 | 48.27 | 30.21 | |
| Human hair | washed: | 40.29 | 47.46 | 32.36 | 4.32 |
| (c) permanent waved | dyed: | 26.64 | 28.98 | 15.94 | |
| Human hair | washed: | 31.97 | 23.72 | 15.79 | 7.49 |
| | | | Average value of ΔE = | | 4.38 |

The present comparative experiments clearly show the improved wash-fastness of the dyed hair colors obtained using the pyrazoles according to the invention, especially on pre-damaged hair.

Unless otherwise indicated, all percentages, are percentages by weight.

The disclosure in German Patent Application 101 09 807.3 of Mar. 1, 2001 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in bridged diaminopyrazoles and dye compositions containing them, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A 4,5-diaminopyrazole compound of formula (I):

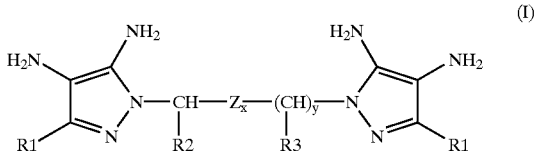

wherein R1 represents hydrogen, a straight-chain or branched $C_1$- to $C_6$-alkyl group, a $C_1$- to $C_4$-hydroxyalkyl group, a $C_1$- to $C_4$-aminoalkyl group, a $C_1$- to $C_8$-alkylamino group, a di($C_1$- to $C_8$-alkyl) amino group, a $C_1$- to $C_4$-alkylamino-($C_1$- to $C_4$-alkyl) group, a di($C_1$- to $C_4$-alkylamino)-$C_1$- to $C_4$-alkyl group or an aryl group;

R2 and R3, independently of each other, are the same or different and each represent hydrogen, a straight-chain or branched $C_1$- to $C_6$-alkyl group, an aryl group, a carboxyl group, an alkoxycarbonyl group, an aminocarbonyl group, a hydroxy group or a $C_1$- to $C_4$-hydroxyalkyl group, or R2 and R3 together represent an unsubstituted $C_1$- to $C_6$-alkylene group;

Z represents a $C_1$- to $C_{10}$-alkyl diradical, which is optionally interrupted by an aromatic diradical; or Z is a diradical of formula —Ar(Alk)$_n$—Ar—, wherein Ar represents an arylene group, Alk represents a —CH$_2$— group and n represents a number from 0 to 6; and x and y independently of each other represent 0 or 1;

or a salt thereof with an organic or an inorganic acid.

2. A 4,5-diaminopyrazole compound selected from the group consisting of bis-(4,5-diamino-pyrazol-1-yl)methane, 1,2-bis-(4,5-diamino-pyrazol-1-yl)ethane, 1,3-bis-(4,5-diaminopyrazol-1-yl)propane, 1,3-bis-(4,5-diamino-3-phenyl-pyrazol-1-yl)propane, 2,3-bis-(4,5-diaminopyrazol-1-yl)propan-1-ol, N-benzyl-2,3-bis-(4,5-diamino-pyrazol-1-yl)propionamide, 1,3-bis-(4,5-diaminopyrazol-1-yl) cyclohexane, 1,4-bis-(4,5-diaminopyrazol-1-yl-methyl)-benzene, 1,4-bis(4,5-diamino-pyrazol-1-yl-methyl)-2,5-dimethoxy-benzene, 1,3-bis(4,5-diaminopyrazol-1-yl-methyl)benzene, 2,6-bis(4,5-diamino-pyrazol-1-yl-methyl)-4-methylphenol, 1,2-bis(4,5-diaminopyrazol-1-yl-methyl) benzene, 1,2-bis-(4,5-diaminopyrazol-1-yl-methyl)-4,5-dimethoxybenzene, 2,3-bis-(4,5-diaminopyrazol-1-yl-methyl)-naphthalene, 2,3-bis-(4,5-diaminopyrazol-1-ylmethyl)anthracene, 9,10-bis-(4,5-diaminopyrazol-1-yl-methyl)anthracene, 4,4'-bis(4,5-diamino-pyrazol-1-yl-methyl)biphenyl and 1,2-bis-[4-(4,5-diamino-pyrazol-1-yl-methyl)phenyl]ethane;

or a salt thereof with an organic or inorganic acid.

3. The 4,5-diaminopyrazole as defined in claim 1, wherein R1 represents said hydrogen, a methyl group or a phenyl group; R2 and R3, independently of each other, each represent said hydrogen, a phenyl group, said aminocarbonyl group or a hydroxymethyl group; Z is an unsubstituted alkylene diradical or a phenylene diradical.

4. The 4,5-diaminopyrazole compound as defined in claim 3, wherein said R1, R2 and R3 each represent said hydrogen.

5. The 4,5-diaminopyrazole compound as defined in claim 1, 2, 3 or 4, wherein said salt is a hydrochloride salt, a sulfuric acid salt, a citric acid salt, or a tartaric acid salt.

6. A dye composition for oxidative dyeing of keratin fibers, wherein said dye composition comprises at least one 4,5-diaminopyrazole compound of formula (I):

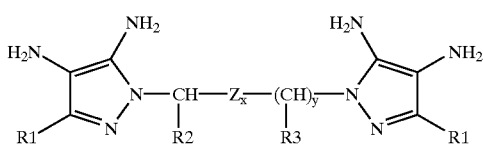

wherein R1 represents hydrogen, a straight-chain or branched $C_1$- to $C_6$-alkyl group, a $C_1$- to $C_4$-hydroxyalkyl group, a $C_1$- to $C_4$-aminoalkyl group, a $C_1$- to $C_8$-alkylamino group, a di($C_1$- to $C_8$-alkyl) amino group, a $C_1$- to $C_4$-alkylamino-($C_1$- to $C_4$-alkyl) group, a di($C_1$- to $C_4$-alkylamino)-$C_1$- to $C_4$-alkyl group or an aryl group;

R2 and R3, independently of each other, are the same or different and each represent hydrogen, a straight-chain or branched $C_1$- to $C_6$-alkyl group, an aryl group, a carboxyl group, an alkoxycarbonyl group, an aminocarbonyl group, a hydroxy group or a $C_1$- to $C_4$-hydroxy-alkyl group, or R2 and R3 together represent an unsubstituted $C_1$- to $C_6$-alkylene group;

Z represents a $C_1$- to $C_{10}$-alkyl diradical, which is optionally interrupted by an aromatic diradical; or Z is a diradical of formula —Ar(Alk)$_n$—Ar—, wherein Ar represents an arylene group, Alk represents a —CH$_2$— group and n represents a number from 0 to 6; and x and y independently of each other represent 0 or 1;

or a salt thereof.

7. A dye composition for oxidative dyeing of keratin fibers, said dye composition comprising at least one 4,5-diaminopyrazole compound selected from the group consisting of bis-(4,5-diaminopyrazol-1-yl)methane, 1,2-bis-(4,5-diamino-pyrazol-1-yl)ethane, 1,3-bis-(4,5-diaminopyrazol-1-yl)propane, 1,3-bis-(4,5-diamino-3-phenyl-pyrazol-1-yl)propane, 2,3-bis-(4,5-diaminopyrazol-1-yl)propan-1-ol, N-benzyl-2,3-bis-(4,5-diamino-pyrazol-1-yl)propionamide, 1,3-bis(4,5-diaminopyrazol-1-yl) cyclohexane, 1,4-bis(4,5-diaminopyrazol-1-yl-methyl) benzene, 1,4-bis(4,5-diaminopyrazol-1-yl-methyl)-2,5-dimethoxy-benzene, 1,3-bis(4,5-diaminopyrazol-1-yl-methyl)benzene, 2,6-bis(4,5-diaminopyrazol-1-yl-methyl)-4-methylphenol, 1,2-bis-(4,5-diaminopyrazol-1-yl-methyl)-benzene, 1,2-bis-(4,5-diaminopyrazol-1-yl-methyl)-4,5-dimethoxy-benzene, 2,3-bis-(4,5-diaminopyrazol-1-yl-methyl)naphthalene, 2,3-bis-(4,5-diaminopyrazol-1-yl-methyl)-anthracene, 9,10-bis-(4,5-diaminopyrazol-1-yl-methyl)biphenyl and 1,2-bis-[4-(4,5-diaminopyrazol-1-yl-methyl)-phenyl]ethane;

or a physiologically compatible salt thereof with an organic or inorganic acid.

8. The dye composition as defined in claim 6 or 7, containing from 0.005 to 20 percent by weight of said at least one 4,5-diaminopyrazole compound.

9. The dye composition as defined in claim 6 or 7, containing from 0.01 to 20 percent by weight of a total amount of coupler substances and developer substances besides said at least one 4,5-diamino-pyrazole compound.

10. The dye composition as defined in claim 6 or 7, further comprising from 0.01 to 10 percent by weight of at least one direct-dyeing dye compound.

11. The dye composition as defined in claim 6 or 7, further comprising water and at least one cosmetic additive ingredient selected from the group consisting of alcohols, surfactants, thickeners and care compounds.

12. A ready-to-apply dye mixture made by mixing a dye composition with an oxidizing composition in a weight ratio of said dye composition to said oxidizing composition of from 5:1 to 1:3, wherein said dye composition comprises at least one 4,5-diaminopyrazole compound of formula (I):

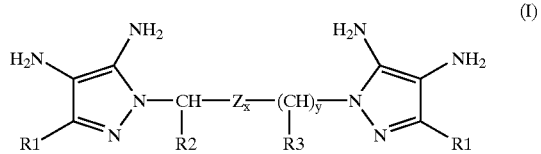

wherein R1 represents hydrogen, a straight-chain or branched $C_1$- to $C_6$-alkyl group, a $C_1$- to $C_4$-hydroxyalkyl group, a $C_1$- to $C_4$-aminoalkyl group, a $C_1$- to $C_8$-alkylamino group, a di($C_1$- to $C_8$-alkyl) amino group, a $C_1$- to $C_4$-alkylamino-($C_1$- to $C_4$-alkyl) group, a di($C_1$- to $C_4$-alkylamino)- $C_1$- to $C_4$-alkyl group or an aryl group;

R2 and R3, independently of each other, are the same or different and each represent hydrogen, a straight-chain or branched $C_1$- to $C_6$-alkyl group, an aryl group, a carboxyl group, an alkoxycarbonyl group, a aminocarbonyl group, a hydroxy group or a $C_1$- to $C_4$-hydroxyalkyl group, or R2 and R3 together represent an unsubstituted $C_1$- to $C_6$-alkylene group;

Z represents a $C_1$- to $C_{10}$-alkyl diradical, which is optionally interrupted by an aromatic diradical; or Z is a diradical of formula —Ar(Alk)$_n$—Ar—, wherein Ar represents an arylene group, Alk represents a —CH$_2$— group and n represents a number from 0 to 6; and x and y independently of each other represent 0 or 1;

or a salt thereof.

13. The ready-to-apply dye mixture as defined in claim 12, having a pH of from 3 to 11.

14. The ready-to-apply dye mixture as defined in claim 12, wherein the dye composition comprises from 0.01 to 10 percent by weight of at least one direct-dyeing dye compound.

15. The ready-to-apply dye mixture as defined in claim 12, wherein the dye composition comprises water and at least one cosmetic additive ingredient selected from the group consisting alcohols, surfactants, thickeners and care compounds.

16. The ready-to-apply dye mixture as defined in claim 12, wherein the dye composition contains from 0.005 to 20 percent by weight of said at least one 4,5-diaminopyrazole compound.

* * * * *